US008940907B2

(12) United States Patent
Gluesenkamp

(10) Patent No.: US 8,940,907 B2
(45) Date of Patent: Jan. 27, 2015

(54) SYNTHESIS OF PHOSPHORIC ESTERS

(75) Inventor: Karl Heinz Gluesenkamp, Essen (DE)

(73) Assignee: Merck Patent GmbH, Darmstadt (DE)

(*) Notice: Subject to any disclaimer, the term of this patent is extended or adjusted under 35 U.S.C. 154(b) by 237 days.

(21) Appl. No.: 13/508,114

(22) PCT Filed: Oct. 8, 2010

(86) PCT No.: PCT/EP2010/006158
§ 371 (c)(1),
(2), (4) Date: May 4, 2012

(87) PCT Pub. No.: WO2011/054429
PCT Pub. Date: May 12, 2011

(65) Prior Publication Data
US 2012/0215006 A1 Aug. 23, 2012

(30) Foreign Application Priority Data
Nov. 5, 2009 (DE) .......................... 10 2009 052 034

(51) Int. Cl.
*C07F 9/09* (2006.01)
*C07F 9/6518* (2006.01)
*C07F 9/6558* (2006.01)
*C07F 9/10* (2006.01)

(52) U.S. Cl.
CPC .............. *C07F 9/65586* (2013.01); *C07F 9/10* (2013.01); *C07F 9/65181* (2013.01)
USPC .............. 548/111; 558/90; 558/166; 558/172

(58) Field of Classification Search
USPC ............................. 548/111; 558/90, 166, 172
See application file for complete search history.

(56) References Cited

U.S. PATENT DOCUMENTS

| 4,956,174 A | 9/1990 | Lang |
| 5,663,405 A | 9/1997 | Ohtani |
| 6,140,496 A | 10/2000 | Benner |

FOREIGN PATENT DOCUMENTS

| EP | 0 486 100 A1 | 5/1992 | |
| JP | 6156191 | 3/1986 | |
| WO | WO 98/55487 | * 12/1998 | ............ C07F 9/6574 |

OTHER PUBLICATIONS

Kraszewski et al. "Phosphoryl Tris-Triazole—A New Phosphorylating Reagent" Tetrahedron Letters, 1980, vol. 21, pp. 2935-2936.*
International Search Report of PCT/EP2010/006158 (Dec. 20, 2010).
English Translation of Japanese Publication No. 61-056191. Publication Date: Mar. 20, 1986. Applicant: Toagosei Chem Ind Co. Ltd., Inventor: Yoshida Masao et al., Application No. 59-176862. Filing Date: Aug. 27, 1984. (Patent Abstracts of Japan).
Scheit, "Die Synthesis von 4-Thiouridin-5'-diphosphat, 4-Thioridin-5'-triphosphat and Desoxy-4-thiothymidin-5'-triphosphat," Chemische Berichte, 101(4):1141-1524 (1968).
Vinogradov et al. "Cross-Linked Polymeric Nanogel Formulations of 5'-Triphosphates of Nucleoside Analogues: Role of the Cellular Membrane in Drug Release," Molecular Pharmaceuticals, 2(6):449-461 (2005).

* cited by examiner

*Primary Examiner* — Joseph Kosack
(74) *Attorney, Agent, or Firm* — Millen, White, Zelano & Branigan, P.C.

(57) ABSTRACT

The present invention relates to a process for the preparation of phosphoric esters, and to selected compounds.

14 Claims, No Drawings

SYNTHESIS OF PHOSPHORIC ESTERS

The present invention relates to a process for the preparation of phosphoric esters, and to selected compounds.

The synthesis building block syn-glycero-3-phosphocholine (GPC) is an important precursor for the synthesis of enantiomerically pure phospho-lipids:

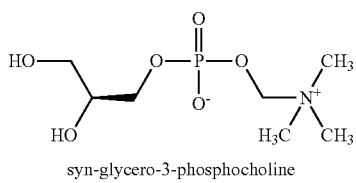

syn-glycero-3-phosphocholine

Thus, GPC is, for example, an important intermediate for the synthesis of pharmaceutically relevant lipids and lipoids. In addition, this substance is employed as medicament for the treatment of Alzheimer's patients, since GPC apparently exerts a normalising effect on damaged nerve tissue. Total syntheses of GPC are known. WO 2007/145476 describes a process for the preparation of GPC with the aid of a reaction of phosphocholine chloride with R-(+)-glycidol. EP 0486100 A1 discloses a process for the preparation of GPC in which firstly isopropylidene glycerol is reacted with 2-chloro-2-oxa-3,3,2-dioxophospholane. Reaction with trimethylamine and hydrolysis of the resultant product gives GPC.

In spite of these known synthetic processes, GPC is usually obtained on a large scale from soya bean/chicken egg lecithins. Isolation from natural sources is apparently cheaper than the known total synthetic variants.

The object of the present invention is therefore the provision of an alternative synthetic method for the preparation of phosphoric esters.

The present invention therefore relates to a process for the preparation of a compound of the formula I

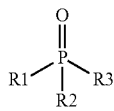

where R1, R2, R3 each stand, independently of one another, for
a) heteroaromatic compounds of the formula II

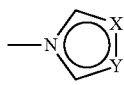

where (—X—Y—) stands for
—CH—CH—CH—,
—Z—CH—CH—,
—CH—Z—CH—,
—CH—CH—Z—,
—CH—Z—,
—Z—CH— or
—Z—Z—,
where Z is in each case selected, independently of one another, from the group O, S, N, NH so as to give an aromatic system, b) —OR4, where R4 stands for a straight-chain or branched alkyl having 1-20 C atoms, a straight-chain or branched alkenyl having 2-20 C atoms and one or more double bonds, a straight-chain or branched alkynyl having 2-20 C atoms and one or more triple bonds, a saturated, partially or fully unsaturated cycloalkyl having 3-24 C atoms, which may be substituted by alkyl groups having 1-6 C atoms, where R4 may be substituted by substituents such as —OR$^1$, —NR$^1_2$, —CN, —C(O)NR$^1_2$, —COOR$^1$, —O(=O)R$^1$, —SO$_2$NR$^1_2$ or aromatic groups, which are optionally provided with conventional protecting groups and in which one or more C atoms may be replaced by heteroatoms, where R$^1$ stands for H, C$_1$- to C$_6$-alkyl, C$_3$- to C$_7$-cycloalkyl, unsubstituted or substituted phenyl,
c) —O$^-$, characterised in that, in a first step, phosphorus oxychloride is reacted with an N-containing heteroaromatic compound, and, in subsequent steps, the heteroaromatic compounds are optionally substituted, at least partially, by compounds having OH functions.

Preference is given to a process in which the compound of the formula I is selected from the formulae Ia, Ib, Ic, Id and Ie:

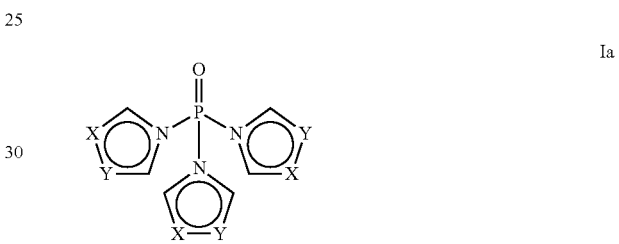

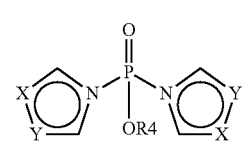

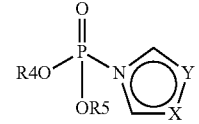

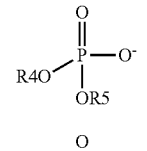

where R5 and R6 each stand, independently of one another and independently of R4, for a straight-chain or branched alkyl having 1-20 C atoms, a straight-chain or branched alkenyl having 2-20 C atoms and one or more double bonds, a straight-chain or branched alkynyl having 2-20 C atoms and one or more triple bonds, a saturated, partially or fully unsaturated cycloalkyl having 3-24 C atoms, which may be substituted by alkyl groups having 1-6 C atoms,
where R5 and R6 may be substituted by substituents such as —OR$^1$, —NR$^1_2$, —CN, —C(O)NR$^1_2$, —COOR$^1$, —C(=O)R$^1$, —SO$_2$NR$^1_2$ or aromatic groups, which are optionally provided with conventional protecting groups and in which one or more C atoms may be replaced by heteroatoms, where $R^1$ stands for H, $C_1$- to $C_6$-alkyl, $C_3$- to $C_7$-cycloalkyl, unsubstituted or substituted phenyl, and where the radicals X, Y and R4 have the meaning as defined above.

A straight-chain or branched alkyl having 1-20 C atoms is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethyl-propyl, hexyl, heptyl, 1-ethylpentyl, octyl, 1-ethylhexyl, nonyl, decyl, undecyl, dodecyl, tridecyl, tetradecyl, pentadecyl, hexadecyl, heptadecyl, octadecyl, nonadecyl or eicosyl.

A straight-chain or branched alkenyl having 2 to 20 C atoms, in which, in addition, a plurality of double bonds may be present, is, for example, allyl, 2- or 3-butenyl, isobutenyl, sec-butenyl, furthermore 4-pentenyl, iso-pentenyl, hexenyl, heptenyl, octenyl, —$C_9H_{17}$, —$C_{10}H_{19}$ to —$C_{20}H_{39}$; preferably allyl, 2- or 3-butenyl, isobutenyl, sec-butenyl, furthermore preferably 4-pentenyl, iso-pentenyl or hexenyl.

A straight-chain or branched alkynyl having 2 to 20 C atoms, in which, in addition, a plurality of triple bonds may be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Saturated or partially or fully unsaturated cycloalkyl groups having 3-24 C atoms are therefore cyclopropyl, cyclobutyl, cyclopentyl, cyclohexyl, cyclo-heptyl, cyclopentenyl, cyclohexenyl, phenyl, cycloheptenyl, each of which may be substituted by $C_1$- to $C_6$-alkyl groups.

Fully unsaturated substituents in the sense of the present invention are also taken to mean aromatic substituents.

Examples thereof are benzyl, phenyl, phenylethyl, phenylpropyl, phenyl-butyl, phenylpentyl or phenylhexyl.

The radicals R4, R5 and R6 are preferably selected, independently of one another, from the group comprising hydrocarbon radicals, which may optionally be substituted by one or more OH functions, sugar radicals, amino acid radicals or nucleic acid radicals.

The radicals R4, R5 and R6 are particularly preferably selected, independently of one another, from

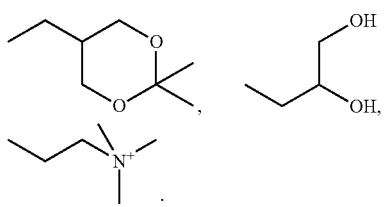

In the first step of the process according to the invention, phosphorus oxychloride is reacted with an N-containing heteroaromatic compound. The heteroaromatic compounds can be selected, for example, from the group comprising

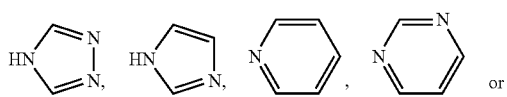

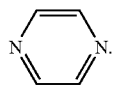

The reaction in the first step of the process according to the invention is preferably carried out in an aprotic solvent.

Particular preference is given to a solvent selected from the group comprising acetonitrile, ethyl acetate, dioxane, tetrahydrofuran, tetramethylsilane, dimethylformamide, dimethyl sulfoxide, acetone, diethyl ether, methyl tert-butyl ether, cyclohexane, dimethylacetamide, sulfolane, N-methylpyrrolidone or dichloromethane.

The solvent is very particularly preferably tetrahydrofuran.

The reaction in the first step of the process according to the invention is furthermore preferably carried out in the presence of an N-containing base, such as, for example, ammonia, primary, secondary or tertiary amines. The base is particularly preferably selected from tertiary alkylamines.

The nitrogen-containing base is very particularly preferably diisopropylethylamine (Hünig base) or triethylamine.

The nitrogen-containing base is particularly preferably triethylamine.

The reaction in the first step of the process described is carried out at room temperature or with cooling. The reaction is preferably carried out at T>0° C. The reaction is particularly preferably carried out at between 10 and 0° C.

In the subsequent steps of the process according to the invention, the heteroaromatic groups may be partially or fully substituted by compounds having OH functions.

The compounds having OH functions are preferably biomolecules or biomolecule derivatives.

Particular preference is given to compounds selected from the group comprising monoalcohols, diols, triols, tetraols, sugars, polyols, OH-containing amino acids or OH-containing nucleic acids.

Very particular preference is given to glycerol or choline derivatives, in particular choline tosylate or isopropylidene glycerol.

The reaction with the OH-containing compound can be carried out at room temperature or reduced temperature. The reaction is preferably carried out at T<0° C., particularly preferably at T<−25° C.

Furthermore, the process according to the invention may include a final synthetic step in which a compound Id is prepared by hydrolysing a

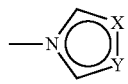

group at pH≥7.

The respective products of the individual steps described above may each be isolated as intermediates. Alternatively, the synthesis can be carried out as a one-pot synthesis. Preference is given to a process for the preparation of the compounds of the formula I in a one-pot process.

Particular preference is given to a process as described above, characterised in that the N-containing aromatic compounds arw

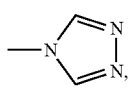

and a compound

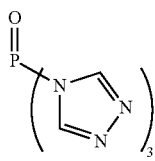

is prepared in the first step.

Especial preference is given to a process, characterised in that the compound of the formula I is syn-glycero-3-phosphocholine.

The process according to the invention thus enables the preparation of syn-glycero-3-phosphocholine. This is illustrated in Scheme 1:

(VIII) is then added, and the adduct (IX) forms, which is subsequently converted in three simple steps into the desired end product GPC (X).

The intermediates in this synthesis can each be isolated or alternatively the reaction sequence can be carried out as a one-pot synthesis.

It is advantageous here that reagent (V) is a very mild phosphorylating reagent. If POCl₃ is used directly, a multiplicity of degradation products is obtained. The chiral synthesis building block (VI) is very acid-sensitive and unsuitable for direct reaction with POCl₃.

The present invention therefore likewise relates to the use of a compound of the formula

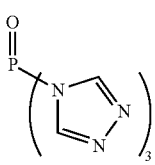

(reagent V) as phosphorylating reagent.

Scheme 1

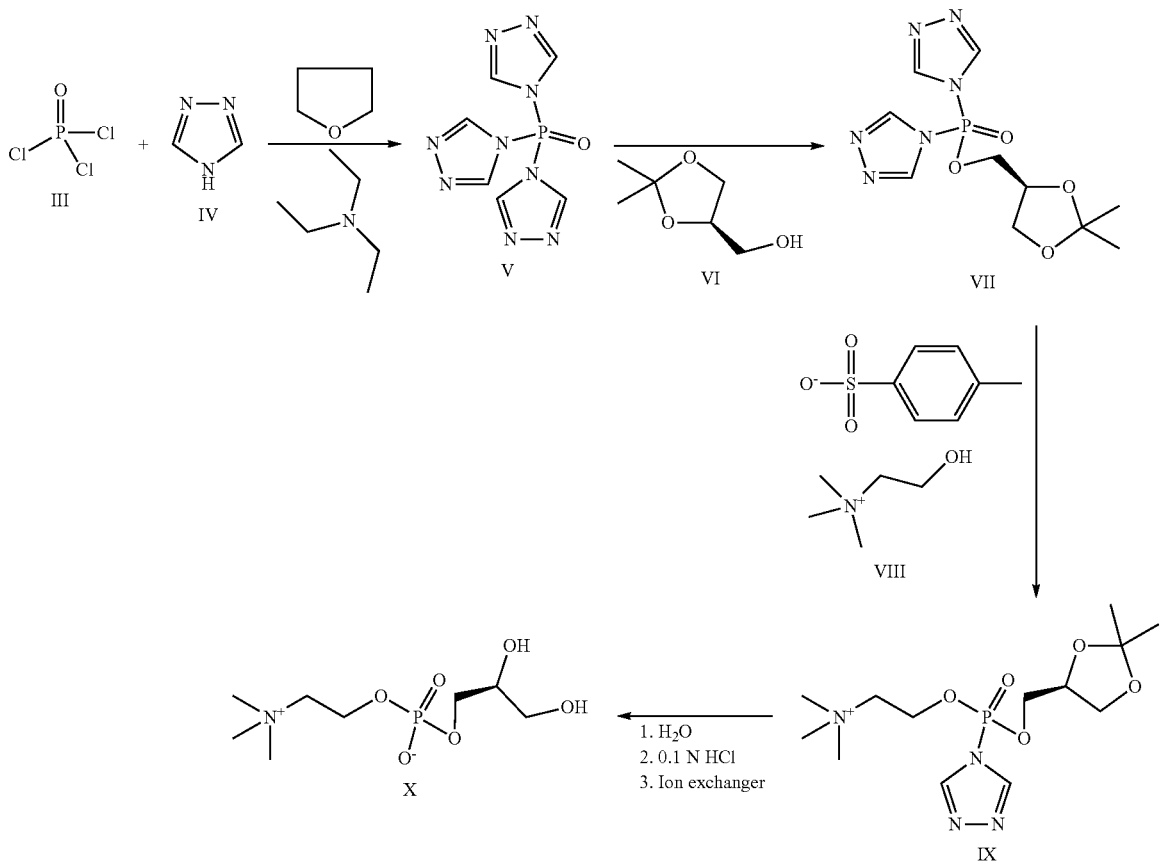

The starting point for this synthesis is the reaction of phosphorus oxychloride (III) with triazole (IV) in the presence of triethylamine to give the phosphorylating reagent (V), which reacts selectively in situ with the chiral synthesis building block (VI) to give the monoester (VII). Choline tosylate In addition, the synthesis described here enables yields of about 70 to more than 90% to be achieved over all steps.

A further advantage consists in that highly pure, crystalline GPC can be obtained.

The present invention furthermore relates to a compound of the formula I as described above, characterised in that the compound is selected from

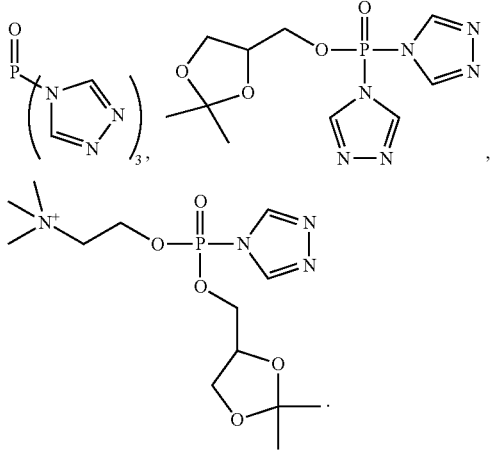

The compounds according to the invention can be prepared with the aid of the process according to the invention and are suitable, for example, as valuable intermediates in the synthesis of pharmaceutical active compounds.

Further compounds which can be prepared with the aid of the process according to the invention are, for example, the compounds of the formulae (1) to (5):

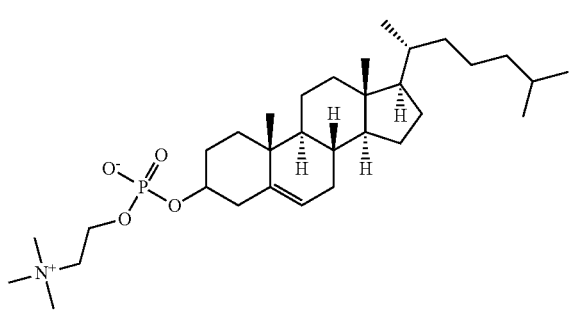

(1)

(2)

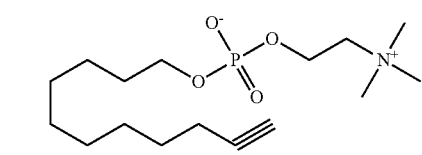

(3)

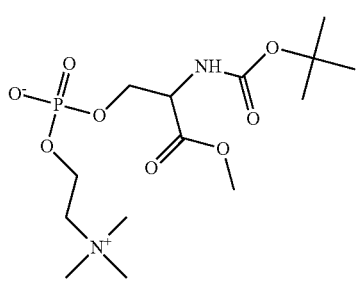

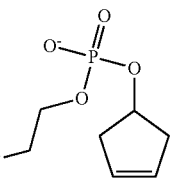

(4)

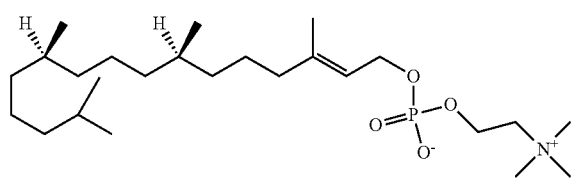

(5)

Cholesterylphosphocholine (1) is a compound known from the literature (Gotoh et al. Chemistry & Biodiversity 2006, 3, 198-209). The amphiphilic substance (1) apparently has a strong influence on the formation dynamics of liposomes.

The compounds of the formulae (2) to (5) can serve as valuable starting materials in the synthesis of a very wide variety of compounds and are therefore likewise a subject-matter of the present invention.

The compound of the formula (2) opens up specific functionalisation of the terminal alkyne, for example with the aid of "click chemistry" introduced by Sharpless.

The orthogonally protected serine derivative of the formula (3) can, for example, be converted directly into novel lipids or lipoids by specific functionalisation.

Compounds of the formula (4) enable the provision of conformationally restricted cyclopentanoid analogues of lipids. After conversion of the compound (4), for example, into a diol derivative, the preparation of a multiplicity of novel lipid compounds is thus conceivable.

The unsaturated phythyl derivative (5) can likewise serve as building block for a multiplicity of novel ether lipids.

The following working examples are intended to explain the invention without limiting it. The invention can be carried out correspondingly throughout the range claimed. Starting from the example, possible variants can also be derived. Thus, the features and conditions of the reactions described in the example can also be applied to other reactions which are not described in detail, but do fall within the scope of protection of the claims.

EXAMPLES

Example 1

Synthesis of Glycerophosphocholine (GPC)

Batch:
25.83 g of isopropylidene glycerol
29.94 g of phosphorus oxychloride
59.31 g of triethylamine+10 g
40.5 g of triazole+2 g
500 ml of THF (dry)
53.79 g of choline tosylate
50 ml of H$_2$O
300 ml of 70% methanol/water
50 ml of 0.1 N HCl
900 g of high-purity Amberlite mixed-bed ion exchanger (Roth)

400 ml of ethanol (absolute)

1 g of $(NH_4)_2MoO_4$ 20 mg of $Ce(IV)SO_4$

10% $H_2SO_4$ 40.5 g (0.564 mol) of triazole in 400 ml of THF are initially introduced in a 2 l glass apparatus under argon, 59.31 g (0.564 mol) of triethylamine are added, and the mixture is stirred at 5-10° C. for 30 min. 29.94 g (0.194 mol) of phosphorus oxychloride in 50 ml of THF (dry) are then added dropwise over a period of 10 min. The temperature during the addition should not rise above 10° C. The suspension is subsequently stirred at 10° C. for a further 2 h. The deposited crystals are filtered, the filtrate is cooled to −10° C., and 25.83 g (0.195 mol) of isopropylidene glycerol, dissolved in 50 ml of THF, are then added dropwise over a period of 1 h. The temperature is kept below 0° C. during the addition. The mixture is then stirred at 0° C.-10° C. for a further 5 h. 53.79 g of ground and dried choline tosylate are subsequently introduced over a period of 10 min, and the suspension is stirred at room temperature for a further 24 h. After addition of 50 ml of $H_2O$, the batch is stirred at room temperature for a further 5 h and left to stand at 4° C. overnight. The precipitate is filtered, and the solution is reduced to 20% in vacuo. 300 ml of 70% methanol/water are added, and the pH is adjusted to 2 using 0.1 N HCl. The solution is subsequently stirred overnight. The solution is then treated with mixed-bed ion exchanger (3×300 g), and the purification is monitored by thin-layer chromatography (Merck silica gel $60F_{254}$) (eluent 70% methanol/water, $R_f$ value GPC=0.25). Spray reagent: $(NH_4)_2MoO_4$ (1 g) and $Ce(IV)SO_4$ (20 mg) are dissolved in 20 ml of 10% $H_2SO_4$. After the plates have been sprayed, they are heated to 150-200° C. In this way, phosphorus compounds are stained blue. After the treatment with ion exchanger, the mixture is evaporated in a rotary evaporator until a clear, viscous oil forms. Repeated evaporation with ethanol at 50° C. in a rotary evaporator firstly forms a crystal slurry, which crystallises out completely after drying in an oil-pump vacuum. Yield: 22 g (45%) of scatterable, extremely hygroscopic, colourless crystals (X in Scheme 1).

$^1$H- and $^{31}$P-NMR Spectra:

Bruker Avance 500 (DRX) spectrometer ($^1$H resonance frequency 500 MHz); solvent, unless indicated otherwise, $CDCl_3$; reference substance $^1$H-NMR: tetramethylsilane as internal standard, $^{31}$P-NMR: phosphoric acid in $D_2O$ as external standard.

$^1$H-NMR of the product glycerophosphocholine (X) in DMSO: 5.60 ppm s, 4.93 ppm s, 4.05 ppm s, 3.65-3.71 ppm m, 3.47-3.53 ppm m, 3.13 ppm s.

Table 1 shows characteristic $^{31}$P-NMR signals of compounds selected as examples, which have been prepared by the above process:

TABLE 1

| $^{31}$P-NMR signals of some phosphoric acid esters | |
|---|---|
| Compound (in Scheme 1) | $^{31}$P-NMR signal (ppm) |
| V | −22.8 |
| VII | −12.2 |
| IX | −6.7 |
| X | 0.04 |

Example 2

Synthesis of Cholesterylphosphocholine

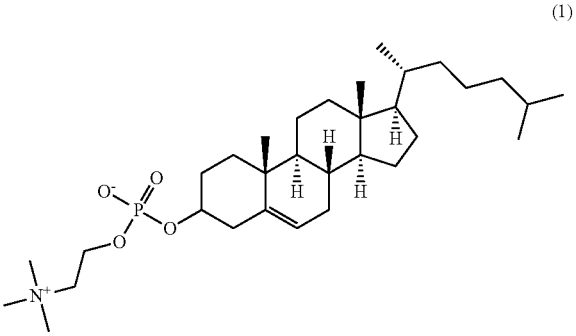

(1)

3.2 g (0.038 mol) of triazole in 0.2 l of chloroform (dry) are initially introduced in a 1 l glass apparatus under argon, 6 g (0.038 mol) of diisopropylethylamine are added, and the mixture is stirred at room temperature for 20 min. The mixture is then cooled to 0° C., and 1.98 g (in 10 ml of chloroform) (0.013 mol) of phosphorus oxychloride are then added dropwise over a period of 30 min. The suspension is subsequently stirred at 0° C. for a further 0.5 h and then cooled to −40° C. 0.5 g of dimethylaminopyridine and 1.66 g (0.013 mol) of diisopropylethylamine are added. 3.7 g (0.129 mol) of choline tosylate are then added in solid form in one portion at −40° C. with vigorous stirring.

The suspension is subsequently stirred for a further 2 h. After 2 h, 5.0 g (0.0129 mol) of cholesterol are introduced at −40° C. over a period of 10 min. The mixture is then stirred at −40° C. for a further 1 h.

200 ml of $H_2O$ are then added, and the mixture is warmed to room temperature. 0.5 l of methyl tert-butyl ether is added to effect phase separation. The organic phase is discarded, and the aqueous phase is washed by shaking a further 3× with chloroform. 0.2 kg of mixed-bed ion exchanger is then added to the aqueous solution, which is then stirred at room temperature for 2 h.

After the treatment with the ion exchanger, the mixture is filtered, and the ion exchanger is washed a further 2× with 70% methanol/water. The combined solutions are evaporated in a rotary evaporator, giving a white solid. The yield is 4.6 g (64%) of cholesterylphosphocholine (1) as scatterable, microcrystalline product.

$^1$H-NMR of the product (500 MHz, $CDCl_3$): δ (ppm)=5.14 (s, br, 1H), 4.05 (s, (br), 1H), 3.70 (m, 1H), 3.39 (m, 2H), 3.05 (s, 9H), 2.0 (m, 2H), 1.80 (m, 3H), 1.50-0.85 (m, 27H), 0.75 (d, j=7 Hz, 3H), 0.69 (d, j=6 Hz, 6H), 0.50 (s, 3H).

Example 3

Synthesis of 2-(trimethylammonio)ethyl undec-10-ynyl phosphate

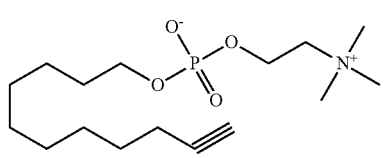

(2)

An analogous procedure to that described in Example 2 gives 3.8 g of 2-(trimethylammonio)ethyl undec-10-ynyl phosphate (2) as amorphous powder. Yield: 71%.

$^1$H-NMR of the product (500 MHz, CDCl$_3$): δ (ppm)=4.29 (s, br, 2H), 3.90 (m, 2H), 3.68 (m, 2H), 3.24 (s, 9H), 2.35 (s, 1H), 2.22 (m, 2H), 1.65 (m, 2H), 1.53 (m, 2H), 1.45-1.3 (m, 10H).

Example 4

Synthesis of 2-(tert-butoxycarbonylaminon)-3-methoxy-3-oxopropyl 2-(trimethylammonio)ethyl phosphate

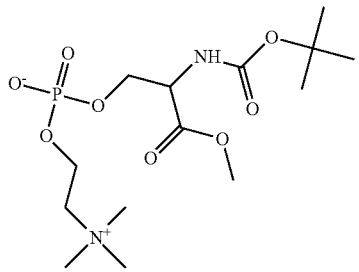

(3)

An analogous procedure to that described in Example 2 gives 3.8 g of 2-(tert-butoxycarbonylaminon)-3-methoxy-3-oxopropyl 2-(trimethylammonio)ethyl phosphate (3) as colourless oil. Yield: 81%.

$^1$H-NMR of the product (500 MHz, CDCl$_3$) δ (ppm)=4.49 (s, br, 1H), 4.28 (m, 3H), 4.15 (m, 1H), 3.67 (m, 2H), 3.36 (s, 9H), 3.36 (s, 3H), 3.23 (s, 9H), 1.46 (s, 9H).

Example 5

Synthesis of cyclopent-3-enyl 2-(trimethylammonio)ethyl phosphate

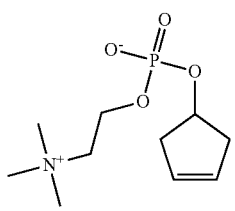

(4)

An analogous procedure to that described in Example 2 gives 2.6 g of cyclopent-3-enyl 2-(trimethylammonio)ethyl phosphate (4) as colourless oil. Yield: 61%.

$^1$H-NMR of the product (500 MHz, CDCl$_3$) δ (ppm)=5.75 (s, 2H), 4.91 (s, 1H), 4.21 (m, 2H), 3.89 (m, 2H), 3.21 (s, 9H), 2.65 (m, 2H), 2.45 (m, 2H).

Example 6

Synthesis of Phythylphosphocholine

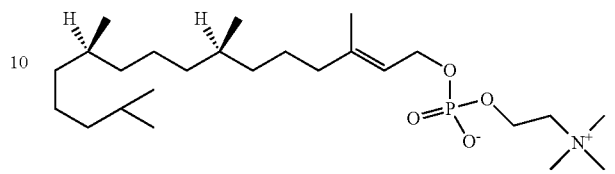

(5)

An analogous procedure to that described in Example 2 gives 1.8 g of phythylphosphocholine (5) as amorphous powder. Yield: 52%.

$^1$H-NMR of the product (500 MHz, CDCl$_3$) δ (ppm)=5.35 (m, 1H), 4.40 (m, 2H), 4.31 (m, 2H), 3.81 (m, 2H), 3.59 (m, 2H), 3.31 (s, 9H), 1.6 (s, 3H), 1.6-0.9 (m, 18H), 0.82 (m, 12H).

The invention claimed is:

1. Process for the preparation of a compound of the formula Id

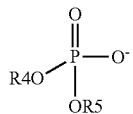

Id where R4 stands for a straight-chain or branched alkyl having 1-20 C atoms, a straight-chain or branched alkenyl having 2-20 C atoms and one or more double bonds, a straight-chain or branched alkynyl having 2-20 C atoms and one or more triple bonds, or a saturated, partially or fully unsaturated cycloalkyl having 3-24 C atoms optionally substituted by alkyl groups having 1-6 C atoms, where R4 is optionally substituted by —OR$^1$, —NR$^1_2$, —CN, —C(O)NR$^1_2$, —COOR$^1$, —C(=O)R$^1$, —SO$_2$NR$^1_2$ or aromatic groups, which are optionally provided with conventional protecting groups and in which one or more C atoms are optionally replaced by heteroatoms, where R$^1$ stands for H, C$_1$- to C$_6$-alkyl, C$_3$- to C$_7$-cycloalkyl, or unsubstituted or substituted phenyl, and R5 stands, independently of R4, for a straight-chain or branched alkyl having 1-20 C atoms, a straight-chain or branched alkenyl having 2-20 C atoms and one or more double bonds, a straight-chain or branched alkynyl having 2-20 C atoms and one or more triple bonds, or a saturated, partially or fully unsaturated cycloalkyl having 3-24 C atoms optionally substituted by alkyl groups having 1-6 C atoms, where R5 is optionally substituted by —OR$^1$, —NR$^1_2$, —CN, —C(O)NR$^1_2$, —COOR$^1$, —C(=O)R$^1$, —SO$_2$NR$^1_2$ or aromatic groups, which are optionally provided with conventional protecting groups and in which one or more C atoms are optionally replaced by heteroatoms, where R$^1$ stands for H, C$_1$- to C$_6$-alkyl, C$_3$- to C$_7$-cycloalkyl or un-substituted or substituted phenyl, characterised in that, in a first step, phosphorus oxychloride is reacted with an N-containing heteroaromatic compound, in subsequent steps, the resulting heteroaromatic compounds are partially substituted by compounds having OH functions to provide the OR4 and OR5 groups, provided that the resulting compound contains one group of the formula II:

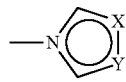

and in a final step the compound Id is prepared by hydrolysing the

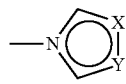

group at pH≥7, where (—X—Y—) stands for
—CH—CH—CH—,
—Z—CH—CH—,
—CH—Z—CH—,
—CH—CH—Z—,
—CH—Z—,
—Z—CH— or
—Z—Z—, where Z is in each case selected, independently of one another, from the group O, S, N, or NH so as to give an aromatic system.

2. Process according to claim 1, characterised in that the reaction in the first step is carried out in an aprotic solvent, preferably selected from the group comprising acetonitrile, ethyl acetate, dioxane, tetrahydrofuran, tetramethylsilane, dimethylformamide, dimethyl sulfoxide, acetone, diethyl ether, methyl tert-butyl ether, cyclohexane, dimethylacetamide, sulfolane, N-methylpyrrolidone and dichloromethane.

3. Process according to claim 1, characterised in that the reaction in the first step is carried out in the presence of an N-containing base, preferably selected from tertiary alkylamines.

4. Process according to claim 1, characterised in that the reaction in the first step is carried out at room temperature or with cooling.

5. Process according to claim 1, characterised in that the compounds having OH functions are biomolecules or biomolecule derivatives.

6. Process according to claim 1, characterised in that the reaction with the compounds having OH functions is carried out at room temperature or reduced temperature.

7. Process according to claim 1, characterised in that the group of the formula II is

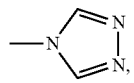

and a compound of the following formula

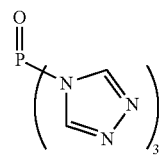

is prepared in the first step.

8. Process according to claim 1, characterised in that the compound of the formula Id is syn-glycero-3-phosphocholine.

9. A compound which is selected from

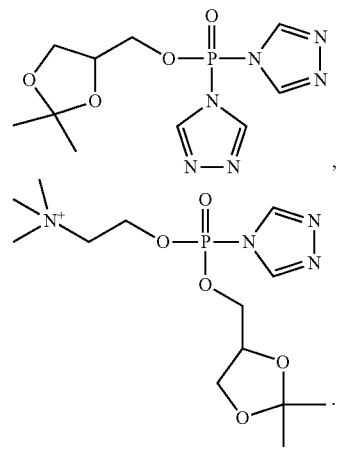

10. Compound selected from the compounds of the formula (2), (3), or (5):

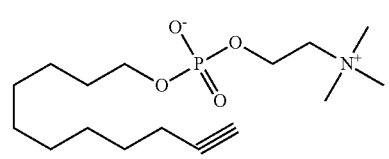

(2)

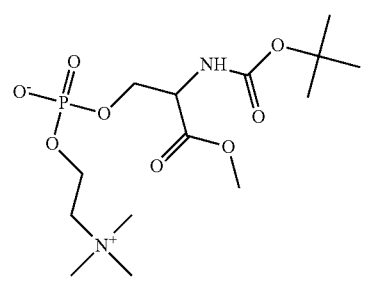

(3)

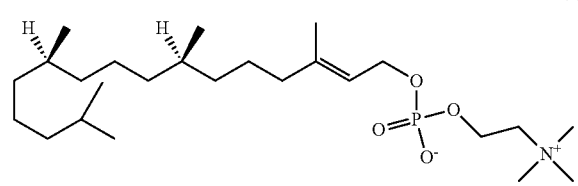

(5)

11. Process according to claim 6, characterised in that the reaction in the first step is carried out with cooling at T>0° C.

12. Process according to claim 1, characterised in that the compounds having OH functions are biomolecules or biomolecule derivatives selected from monoalcohols, diols, triols, tetraols, sugars, polyols, OH-containing amino acids or OH-containing nucleic acids.

13. Process according to claim 1, characterised in that the reaction with the compounds having OH functions is carried out at reduced temperature of T<0° C.

14. Process according to claim 1, characterised in that the reaction with the compounds having OH functions is carried out at reduced temperature of T T<−25° C.

* * * * *